(12) United States Patent
Doyle

(10) Patent No.: US 6,795,177 B2
(45) Date of Patent: Sep. 21, 2004

(54) MULTIPASS SAMPLING SYSTEM FOR RAMAN SPECTROSCOPY

(75) Inventor: Walter M. Doyle, Laguna Niguel, CA (US)

(73) Assignee: Axiom Analytical, Inc., Irvine, CA (US)

(*) Notice: Subject to any disclaimer, the term of this patent is extended or adjusted under 35 U.S.C. 154(b) by 128 days.

(21) Appl. No.: 10/285,768

(22) Filed: Nov. 1, 2002

(65) Prior Publication Data

US 2003/0081206 A1 May 1, 2003

Related U.S. Application Data

(60) Provisional application No. 60/335,473, filed on Nov. 1, 2001.

(51) Int. Cl.[7] .................................................. G01J 3/44
(52) U.S. Cl. ..................................................... 356/301
(58) Field of Search .................................. 356/301, 311

(56) References Cited

U.S. PATENT DOCUMENTS

| | | | | |
|---|---|---|---|---|
| 2,779,230 A | * | 1/1957 | White ........................ | 356/301 |
| 3,556,659 A | * | 1/1971 | Halls ......................... | 356/301 |
| 4,345,837 A | * | 8/1982 | Kallet ........................ | 356/301 |
| 4,953,976 A | * | 9/1990 | Adler-Golden et al. ..... | 356/301 |
| 5,112,127 A | * | 5/1992 | Carrabba et al. ........... | 356/301 |
| 5,194,913 A | * | 3/1993 | Myrick et al. .............. | 356/301 |
| 5,753,449 A | * | 5/1998 | Yamaguchi et al. ........ | 356/301 |

* cited by examiner

*Primary Examiner*—F. L. Evans
*Assistant Examiner*—Kara Geisel
(74) *Attorney, Agent, or Firm*—Myers Dawes Andras & Sherman LLP; Joseph C. Andres

(57) ABSTRACT

A multipass system for sampling by Raman spectroscopy enhances the collected signal and provides a system having improved sensitivity. The system incorporates an injection element for inserting collimated excitation radiation into an optical path, an objective lens for focusing the excitation radiation into the sample and for collecting radiation, a blocking filter that is substantially perpendicular to the optical path and that transmits Raman shifted radiation and reflects the excitation radiation, and a mirror for causing the excitation radiation to reflect excitation radiation back and forth between the mirror and the blocking filter multiple times while Raman shifted radiation is passed through the blocking filter for collection and analysis.

19 Claims, 10 Drawing Sheets

PRIOR ART RFP-410 RAMAN PROBE

PRIOR ART RFP-420 RAMAN PROBE

PRIOR ART RFP-480 RAMAN PROBE

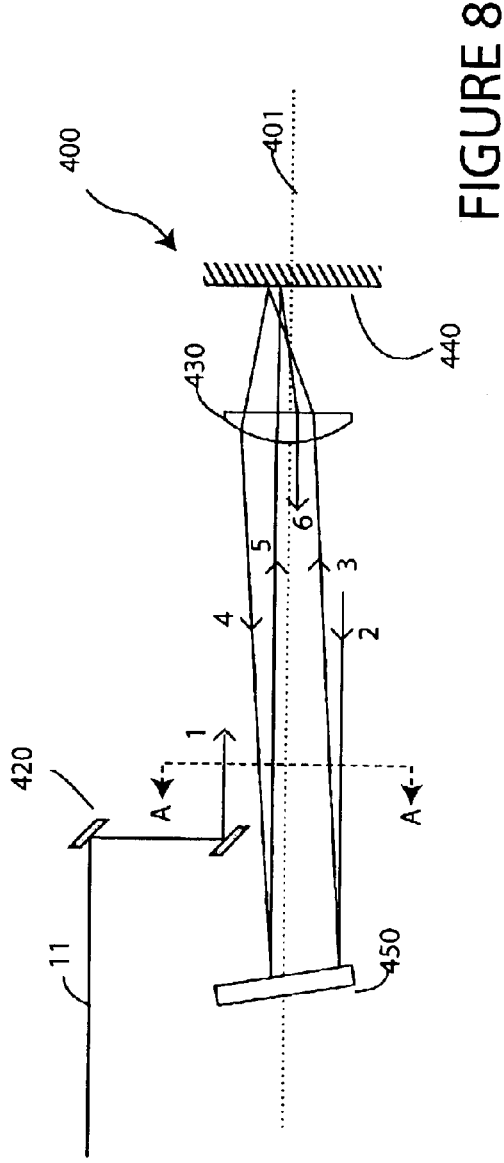
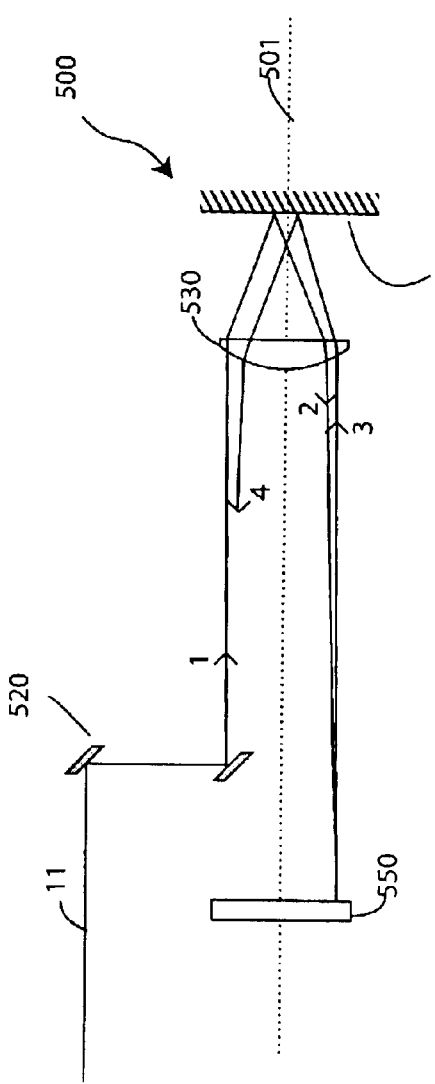
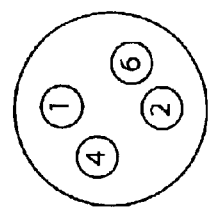
FIGURE 8
FIGURE 8A
FIGURE 9

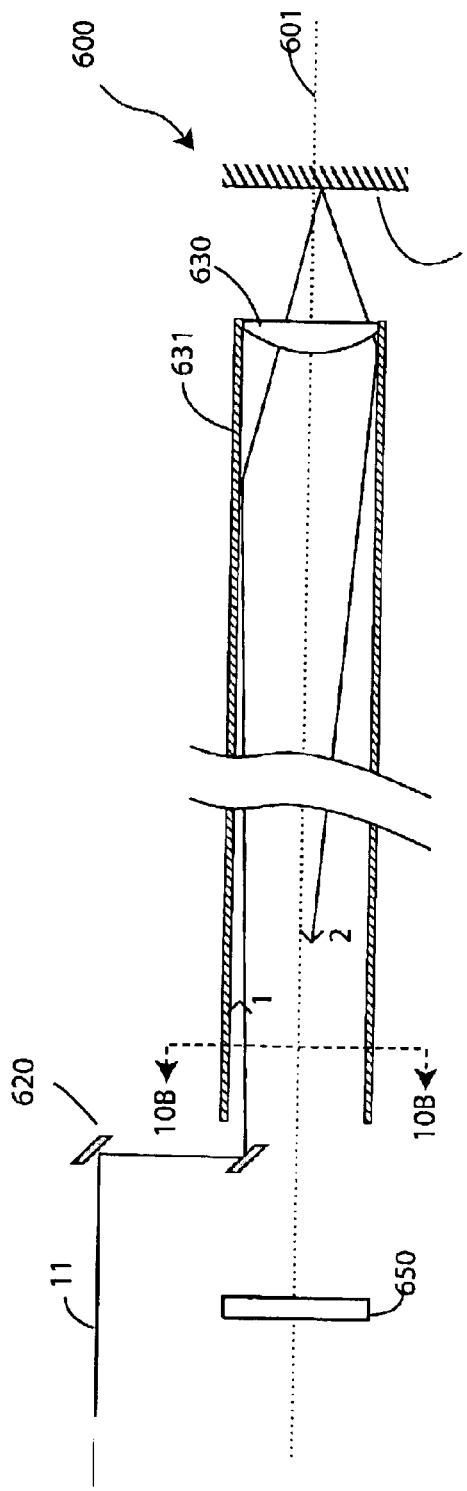
FIGURE 10A
FIGURE 10B
FIGURE 10C

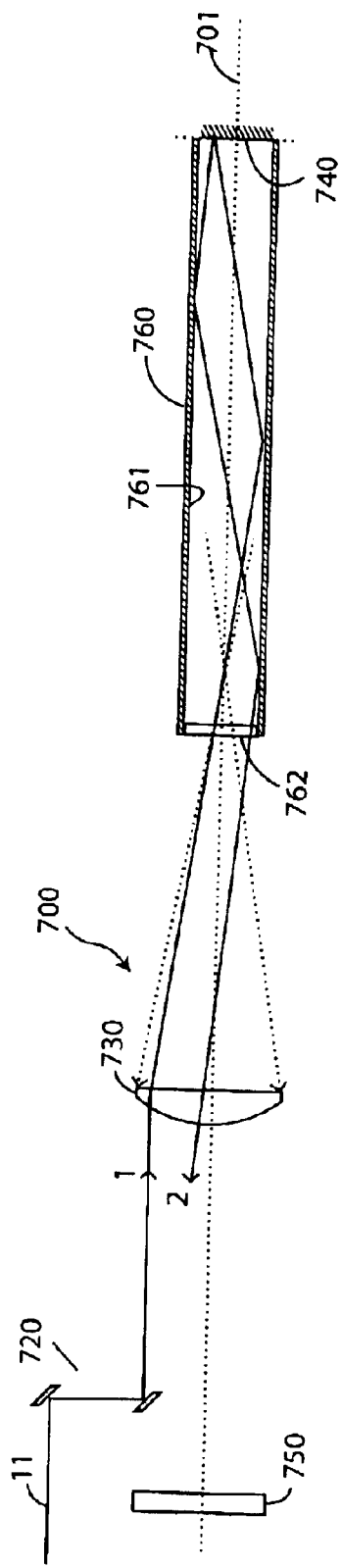
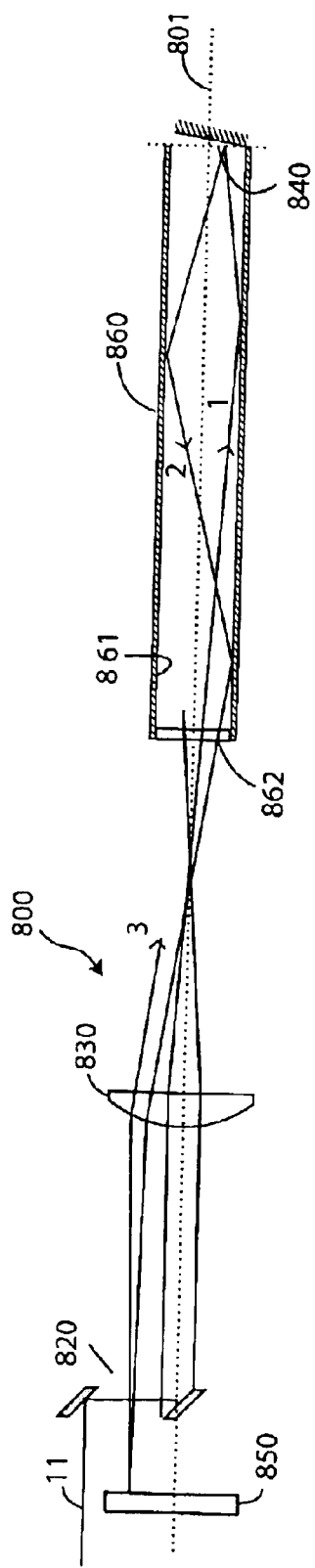

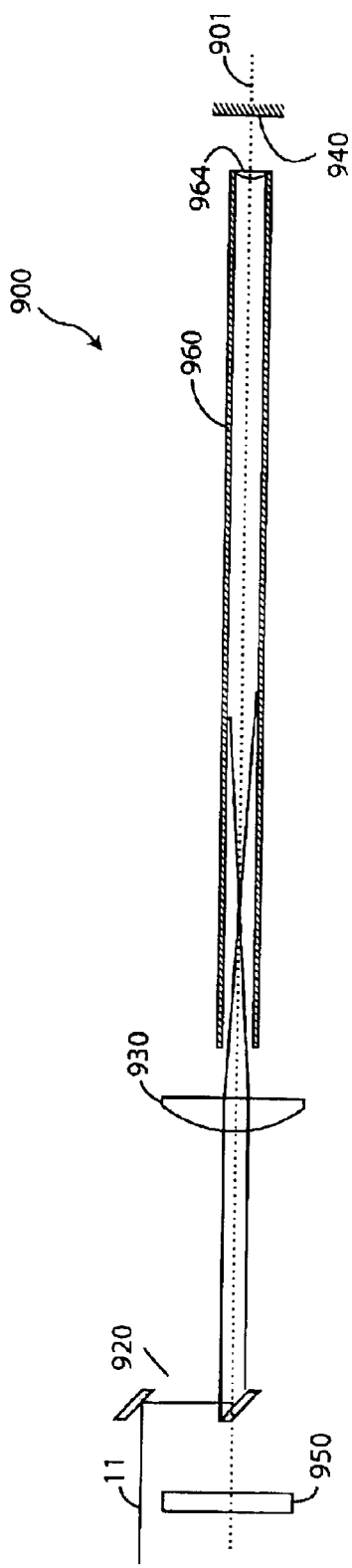
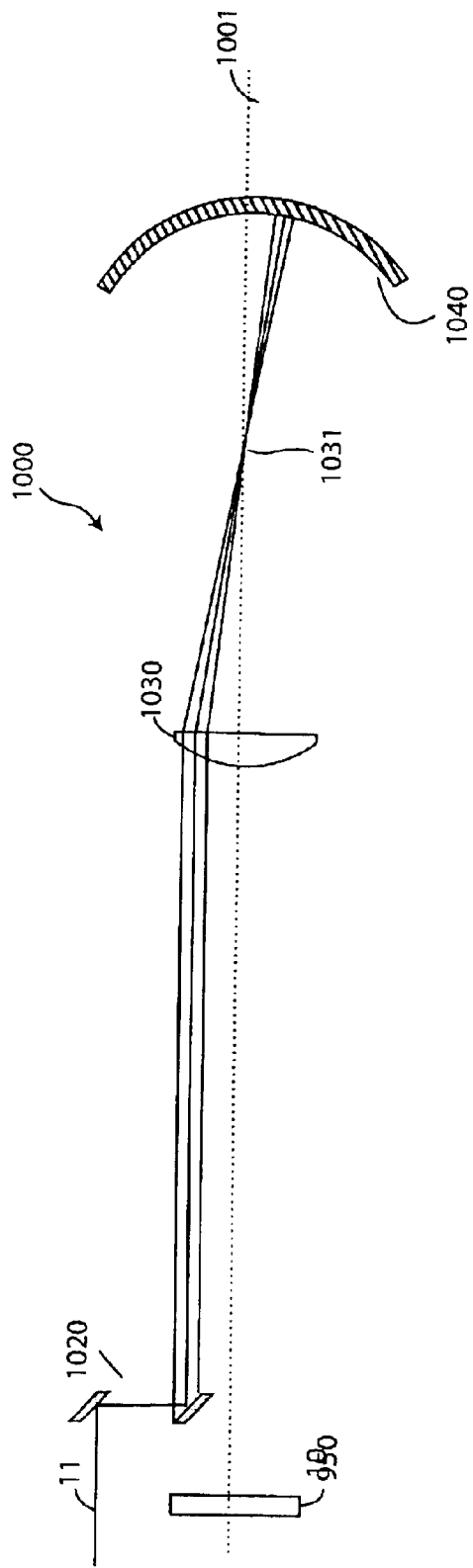

MULTIPASS SAMPLING SYSTEM FOR RAMAN SPECTROSCOPY

This application claims the benefit of provisional application serial No. 60/335,473, filed Nov. 1, 2001, the specification of which is incorporated herein by reference in its entirety.

FIELD OF THE INVENTION

The instant invention lies generally in the field of spectroscopy, and specifically in the field of Raman scattering spectroscopy.

BACKGROUND

Molecular spectroscopy is a family of analytical techniques that provide information about molecular structure by studying the interaction of electromagnetic radiation with the materials of interest. In most of these techniques, the information is generally obtained by studying the absorption of radiation as a function of optical frequency.

Raman spectroscopy is unique in that it analyzes the radiation that is emitted (or scattered) when the sample is irradiated by an intense optical signal consisting of a single frequency, or a narrow range of frequencies. FIG. 1 is a simplified view of a typical application of Raman spectroscopy. As shown, a laser source 10 outputs an excitation beam 11 that intensely irradiates a sample that is contained within a sample cell or a flow cell 12. Note that the laser's excitation radiation 11 is shown as a solid line. As further shown by dashed lines 13, some Raman scattering of variously shifted wavelengths occurs due to the laser light's Raman interaction with the sample's molecular bonds. As shown by more solid lines 14, however, a great deal more Rayleigh scattering occurs at the original laser frequency due to the laser's interaction with the atoms as opposed to with the bonds. In the typical system, a long pass laser rejection filter, or simply blocking filter 20, blocks the Rayleigh scattering (solid lines 14) while passing the Raman scattering (dashed lines 13, 15) on to a spectrometer 31 for detection and analysis (typically with the assistance of a separate general purpose computer 32 as shown).

As described above, the "Raman scattering" signal is essentially an emission spectrum with frequency dependent intensities. The individual bands in this spectrum are shifted from the frequency of the excitation signal by amounts that are related to the structure of the molecules present in the sample.

Modern Raman spectrometers typically use powerful single wavelength lasers as the source of excitation radiation. Nonetheless, Raman scattering is an extremely rare event, so very little of the laser radiation is actually converted to Raman shifted energy. Most of it simply travels on through the sample without interaction, or is Rayleigh scattered by the sample without having its frequency altered. The weakness of the Raman signal is in part offset by the very high sensitivity of the visible and infrared detectors used. However, it is important to minimize the amount of reflected or Rayleigh scattered laser radiation that gets into the receiving optics since this can swamp the detector either on its own or by generating fluorescence and/or Raman radiation in the receiving optics.

Most sample interfacing systems currently being used in Raman spectroscopy employ optical filters to separate the excitation signal from the Raman shifted signal being studied. Some examples are given in I. R. Lewis & P. R. Griffiths, "Raman Spectroscopy with Fiber-Optic Sampling", *Applied Spectroscopy*. Vol. 50, pg. 12A, 1996, FIGS. 5 through 11. (Also see U.S. Pat. Nos. 5,112,127 and 5,377,004.) In most of these designs, a dichroic filter inclined to the axis of the optical path combines the transmitted and received paths. In at least one case (FIG. 5,*b* of Ref. 1), the transmitted and received paths are inclined at an angle to each other.

Mirrors have been proposed for enhancing Raman radiation signal levels in Raman Spectroscopy, but the enhancement provided by the embodiments known to the inventor do not provide as much gain as is possible with the present invention. In "Raman Spectroscopy for Chemical Analysis", Wiley Interscience, New York, N.Y. 2000, pg. 121, for example, Richard L. McCreery reported an enhancement in the collected signal by providing two passes of excitation radiation by reflecting the excitation radiation back through the sample. The enhancement of signal levels is due to two factors: (1) the increased laser radiation intensity caused by folding the beam back through the sample; and (2) the fact that the mirror facilitates the collection of forward scattered Raman radiation as well as back scattered radiation. While signal levels have been improved by this method, the inventor has found that it is less than double. The enhancement is reduced by the fact that only half of the focal region is available for interaction of the beam with the sample.

There remains a need, therefore, for a Raman spectroscopy system that provides significantly increased Raman radiation signal levels beyond those currently available.

FIGS. 2–4 depict three different versions 50, 60, 70 of the RFP-400 Series Raman probes manufactured by the inventor and disclosed in the provisional application referred to above. As shown, all three probes 50, 60, 70 are based on a unique design in which the transmitted excitation beam 11 is injected along a path which is parallel to the received collection beam 15 by means of a small reflecting optical element such as a mirror or rhomboid 54, 64, 74. As a result, the long pass filter 57, 67, 77 used to eliminate the laser signal from the receiving optics can be perpendicular to the path 15. The illustrated probes 50, 60, 70 are not multi-pass probes. The characteristics of the RFP-400 design shown in FIGS. 2–4, however, pave the way for the unique family of enhancements that are the subject of this application.

SUMMARY OF THE INVENTION

The preferred embodiments of the present invention take advantage of the facts that:

1. The difference between the laser excitation frequency and the frequencies of the Raman shifted radiation;
2. The fact that Raman scattering events are rare whereby very little excitation radiation is lost on each pass through the sample;
3. The fact that most interference filters are highly reflecting at frequencies there they block the laser signal from being transmitted; and
4. The fact that many samples are highly transparent in the frequency range characteristic of the Raman shifted radiation.

Each of the embodiments includes the following elements:

1. The use of a laser frequency blocking filter approximately perpendicular to the axis of the optical system;
2. A lens or other focusing device positioned in the common transmitted and received optical path so as to focus the laser radiation into a small region within the sample and, at the same time, collect Raman scattered radiation from this region;

3. A mirror within or behind the sample to be analyzed positioned so as to reflect the transmitted laser signal back through the sample so that at least a portion of it strikes the blocking filter at approximately normal incidence;

4. A means for injecting the laser signal into the optical path between the blocking filter and the lens so as to obscure only a minor portion of the receiving optical path.

The invention may be regarded as a multi-pass Raman sampling system that illuminates a sample with laser excitation radiation to produce Raman shifted radiation, the system comprising: an injection element located in an optical path, the injection element obscuring only a portion of the optical path while injecting a substantially collimated beam of laser excitation radiation toward the sample in a first direction; an objective lens positioned in the optical path and defining an optical axis and a focal point, the objective lens focusing the collimated beam of laser excitation radiation traveling in the first direction into the sample to produce Raman shifted radiation, the objective lens collecting radiation that is emanating from at or near the focal point and then transmitting the radiation into the optical path in a second direction that is substantially opposite to the first direction; a mirror located within or behind the sample at or near the focal point, the mirror reflecting both laser excitation radiation and Raman shifted radiation back through the sample toward the objective lens and the injection element in the second opposite direction; a blocking filter located optically beyond the injection element such that the injection element is in the optical path between the objective lens and the blocking filter, the blocking filter being substantially reflective to the laser excitation radiation and substantially transparent to the Raman shifted radiation, the blocking filter passing the Raman shifted radiation out of the system for analysis and reflecting the laser excitation radiation back in the first direction toward the objective lens, the sample, and the mirror; and signal enhancement means for causing at least a portion of the laser excitation radiation that is reflected by the mirror to miss the injection element and strike the blocking filter where it is reflected back to the sample through the objective lens to produce more Raman shifted radiation. The just summarized invention is best understood with reference to the following drawings taken together with the accompanying description.

BRIEF DESCRIPTION OF THE DRAWINGS

FIG. 8 is a diagrammatic view of a multi-pass Raman sampling system 400 that includes an offset injection element 420 and a tilted blocking filter 450;

FIG. 8A shows the approximate intersections of ray paths 1, 2, 4 and 6 when FIG. 8 is viewed along section lines A—A;

FIG. 9 is a diagrammatic view of a multi-pass Raman sampling system 500 that includes an offset and titled injection element 520;

FIG. 10A is a diagrammatic view of a multi-pass Raman sampling system 600 that uses a long lightguide 631;

FIG. 10B is a diagrammatic section view taken along lines 10B—10B showing how reflections from the inner walls of the light guide 631 will create a curved arc 632 of illumination;

FIG. 10C is a diagrammatic view corresponding to FIG. 10B showing how multiple passes will create an annular ring 633 of illumination, only a portion of which will be blocked by the injection element;

FIG. 11 is a diagrammatic view of a multi-pass Raman sampling system 700 that includes an offset injection element 720 in combination with a sample cell 760 in the form of a hollow light guide 761 with a window 762 and a perpendicular end mirror 740;

FIG. 12 is a diagrammatic view of a multi-pass Raman sampling system 800 that includes a sample cell 860 in the form of a hollow light guide 861 with a window 862 and a tilted end mirror 840;

FIG. 13 is a diagrammatic view of a multi-pass Raman sampling system 900 that includes a small diameter probe tip of the type illustrated in FIG. 3;

FIG. 14 is a diagrammatic view of a multi-pass Raman sampling system 1000 that includes a concave spherical mirror 1040;

DETAILED DESCRIPTION OF THE PREFERRED EMBODIMENTS

Figure 1:
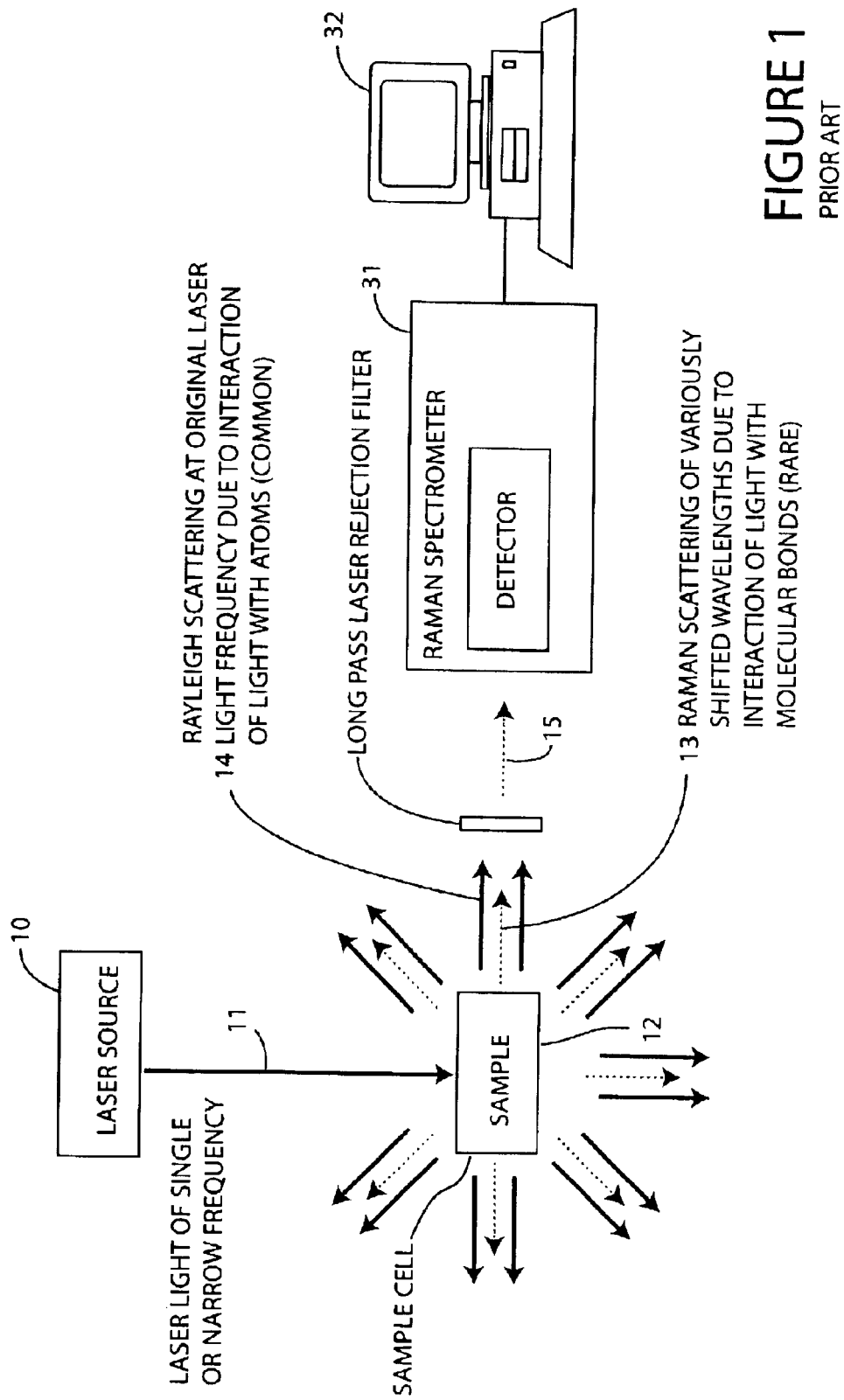
FIG. 1 is a simplified view of conventional Raman spectroscopy.
Figure 2:
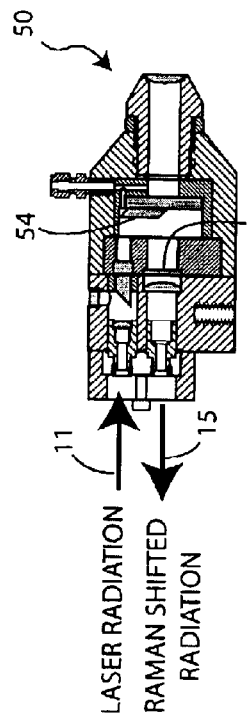
FIG. 2 is a sectional view of a first prior art Raman probe.
Figure 5:
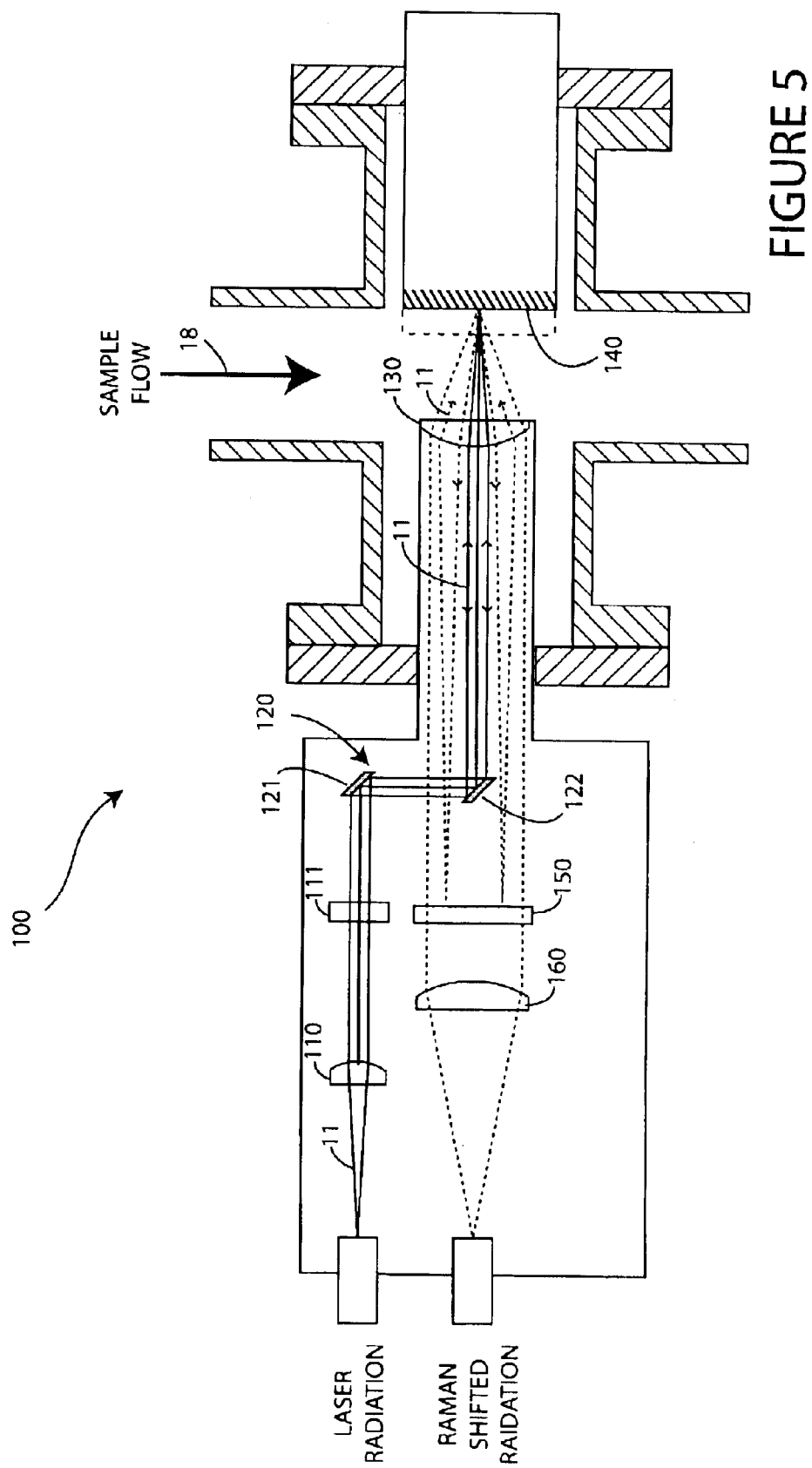
FIG. 5 is a diagrammatic view of a first preferred multi-pass Raman sampling system 100 constructed in accordance with this invention.

FIG. 5 is a diagrammatic view of a first preferred multi-pass Raman sampling system 100 constructed in accordance with this invention. The illustrated system 100 uses the standard design of Axiom Analytical's Model RFP-410 probe (FIG. 2), and adds a flat mirror 140 located within or behind the sample and positioned approximately at the focal point of the lens 130. As shown, the laser radiation 11 diverging from the end of an optical fiber is initially collimated by a collimating lens 110 and then passed through a bandpass filter 111. The laser radiation 11 is then injected into the optical path with an injection element 120 (shown here as a pair of angled mirrors 121, 122) and finally focused into the sample flow 18 and onto the mirror 140 with an objective lens 130. Raman shifted radiation and Raleigh scattered radiation will travel along the optical path and ultimately impinge upon the blocking filter 150. The Raman radiation 15, as suggested by FIG. 1, will pass through the blocking filter 150 and, thereafter, be focused into a fiber-optic cable with a lens 160.

In the case where the laser radiation 11 is perfectly collimated and the mirror 140 is positioned exactly in the focus and perpendicular to the optical axis 101 (as shown in solid lines), the laser signal 11 reflected by the mirror 140 will be recollimated by the lens 130 and directed back to the optical injection element 120. In this case, none of the laser radiation 11 reflected by the mirror 140 will reach the blocking filter 150.

In practice, however, the laser beam 11 is not perfectly collimated, but instead has an inherent beam spread. Furthermore, various means for enhancing the signal may be employed, such as moving the mirror 140 slightly out of the focal plane of the lens 130 can increase the beam spread of the reflected laser signal. This is illustrated by the dashed lines in FIG. 5. Optical beam spread, whether inherent or induced, will enable some portion of the reflected laser signal to be reflected by the blocking filter 150. Once reflected, it will be refocused by the lens 130 into the sample 18, where it can generate more Raman shifted radiation.

Depending on the dimensions of the various elements, some of this second pass laser radiation (shown with dashed lines for clarity) can again be directed back to the blocking filter where it can again be reflected and again be focused into the sample. With the configuration shown in FIG. 5, it is doubtful that much of the radiation will make more than three round-trip passes through the sample.

Figure 6A:
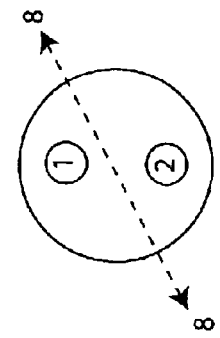
FIG. 6A is a cross-section of FIG. 6 taken along section lines A—A.
Figure 6:
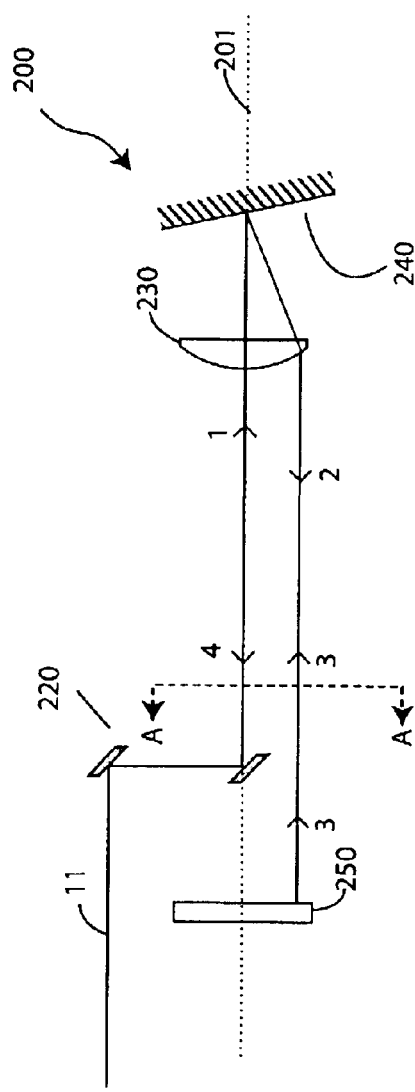
FIG. 6 is a diagrammatic view of a multi-pass Raman sampling system 200 that includes a slightly tilted mirror 240.

FIG. 6 provides a variation on the configuration of FIG. 5. In both case, the injection elements 120, 220 are on the optical axis 101, 201. In the embodiment of FIG. 6, however, a different enhancing means is employed. In particular, the mirror 240 is tilted slightly so that the returned signal misses the injection element 220 completely. In this case, nearly all of the laser signal 11 can make two round trip passes through the sample before returning to the injection element 220. Again, slightly defocusing the position of the mirror will allow a portion of the returning beam to miss the injection element on this pass, allowing it to undergo additional passes through the sample.

In studying FIGS. 5 and 6, it should be noted that the presence of a mirror 140 or 240 at the focal point would lead to some enhancement of the Raman signal even if reflection from the blocking filter 150, 250 were not employed. In practice, however, it has been found that the enhancement obtained in this case is generally well under a factor of two. In contrast, the reflection from the blocking filter 150, 250 used in the preferred embodiments of this invention typically produces the unexpected results of enhancements ranging between factors of four and ten.

Figure 7:
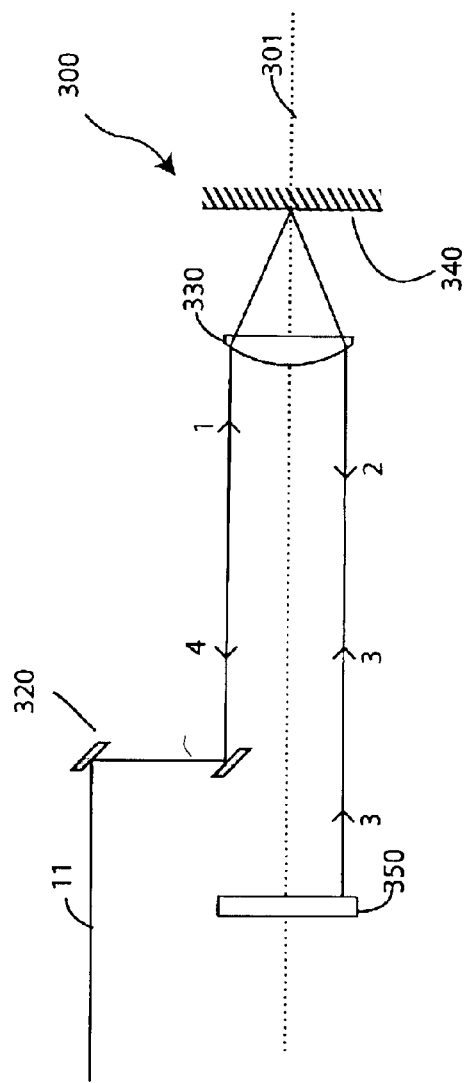
FIG. 7 is a diagrammatic view of a multi-pass Raman sampling system 300 that includes an offset injection element 320.

FIG. 7 is another variation on FIG. 5. Here, the injection element 320 is offset from the optical axis 301. In this case, it is not necessary to tilt the return mirror 340. The first return pass (pass number 2) will be displaced on the opposite side of the axis 301 an equal amount and hence will not strike the injection element 320. The second return pass (pass number 4) will again strike the injection element 320 if the laser signal 11 is perfectly collimated.

FIG. 8 illustrates an embodiment of a fourth system 400 that enables the laser signal 11 to make more than four passes through the sample without striking the injection element 450. This embodiment is similar to the design illustrated by the system 300 of FIG. 7 in that both use a injection element that is offset from the optical axis. The FIG. 8 system 400, however, further includes the concept of tilting the blocking filter 450. The effect of tilting the blocking filter 450 can be best understood by referencing FIG. 6A which is a cross-section of FIG. 6 taken along section lines A—A in FIG. 6. The FIG. 6A section shows the location of the first two passes in the region of this cross section where, as in FIG. 6, the blocking filter 25 is not tilted. With reference to FIGS. 6 and 6A, consider now the effect of tilting the blocking filter 450 (250) about the axis indi-cated by 8—8. In such case, the projections of ray paths 1 through 6 in this plane of 8-8 appears as shown in FIG. 8 We can see that, for the dimensions illustrated, return path 4 falls closer to the axis than the injection element 420 and thus misses it. Like path 2, path 6 will fall on the other side of the axis 401 from the injection element 420. It is contemplated that the dimensions can be chosen so that even more passes will be possible without striking the injection element 420. FIG. 8A shows the approximate intersections of ray paths 1, 2, 4 and 6 when FIG. 8 is viewed along section lines A—A.

The FIG. 8 design involve two regions of interaction between the radiation and the sample, one on-axis and one slightly displaced. Incident beams 1, 5, 9, etc. will focus on-axis. Beams 3, 7, 11, etc. will focus at a common point off-axis. In order for both of these regions to contribute to the received or collected signal, the separation between them must be smaller than the radius of the projection of the collection fiber in the sample plane. In order to accomplish this, it will be necessary for the distance between the lens and the injection element to be substantially greater than the focal length of the lens. Different ratios may be employed for varying degrees of benefit. However, locating the lens away from the injection element a distance of a factor of ten or greater relative to the focal length of the lens is believed reasonable for this purpose.

FIG. 9 illustrates a system 500 having a configuration in which the reflex mirror 540 and blocking filter 550 remain perpendicular to the central axis 501 of the system, but the injection element 520 is tilted slightly. When the injection element 520 is tilted in the same plane as its offset from the axis (as shown in the illustration), the fourth pass returns to approximately the same region as the insertion element 520. In this case, tilting the element may not provide any benefit over the non-tilted case shown in FIG. 6. However, if the injection element 520 is tilted about a different axis (such as one at 45 deg. to the offset plane), path 4 will return out of the offset plane and miss the injection element 520. It thus can be seen that this configuration will provide similar benefits to that illustrated by FIG. 8.

A lightguide may be desirable in certain circumstances. With any of the configurations discussed so far, as the distance between the injection element 120-520 and the objective lens 130-530 is increased, the inherent beam spread will result in some of the radiation 11 falling outside of the area of the objective lens 130-530. This tendency can be reduced by placing a lightguide in the region between the injection element 120-520 and the objective lens 130-530. This approach is employed in Axiom Analytical's longer probes, such as the RFP-480 illustrated in FIG. 3.

FIG. 10A shows a system 600 that uses a long lightguide 631. As suggested above, a lightguide in conjunction with a reflex mirror 640 can provide an additional benefit. In FIG. 10A, the injection element 620 is tilted. If the light guide 640 is long enough, the laser beam 11 emerging from the tilted element 620 will eventually strike the inside of the light guide 631 before striking the objective lens 630. Since the light emerging from the injection element 620 is not perfectly collimated, but rather a diverging bundle, the image in the plane of the reflex mirror 630 will not be a point, but rather a spot.

In the absence of reflection within the light guide 631, the spot would be a round spot of finite area. However, after reflection from the inner walls of the light guide 631, the spot will tend to form a curved arc 632 with the center of curvature on the system central axis 601 as shown in FIG. 10B. Tilting the injection element 420 out of the plane of offset will accentuate this effect by creating a higher percentage of skew rays. The net effect, after several passes, will be an annular ring or circle 633 of illumination centered on the axis 601 as shown in FIG. 10C. Significantly, only a small percentage of the rays which give rise to this circle 633 will intersect the position of the injection element 620.

FIGS. 11 and 12 show two embodiments 700, 800 in which the subject invention is combined with a sample cell 760, 860 in the form of a hollow light guide 761, 861 with a window 762, 862 on one end and a mirror 740, 840 on the other. The cell 760, 860 would generally be provided with flow fittings (not shown) to allow continuous flow of a liquid or gas. In FIG. 11, the injection element 720 is mounted off of the central axis 701 and is furthermore to be tilted in a plane other than the offset plane. As a result, the excitation radiation will be in the form of a bundle of skew rays. After a few reflections from the walls and reflection from the end mirror 740, 840, the radiation will be in the form of an annular bundle of rays similar to that shown in FIG. 10C. Most of this bundle arrays will miss the injection element 720, 820.

In FIG. 11, the injection element 720 is placed on axis. In this case, we can rely on the inherent spread of the beam to fill the light guide 760, resulting in a larger bundle of rays on return, some percentage of which will miss the injection element 720. Alternatively, we can either slightly taper the lightguide 760 to provide a tapered sample cell, or we can tilt the end mirror 740 (as shown). In either case, the divergence of the excitation beam will be increased, resulting in much of the beam missing the injection element 720.

From the two examples of the sample cells 760, 860 of FIGS. 11 and 12, it can be seen that most of the techniques discussed above can be combined with a lightguide type sample cell 760, 860 to provide multiple passes through the sample and enhanced sensitivity.

Figure 3:
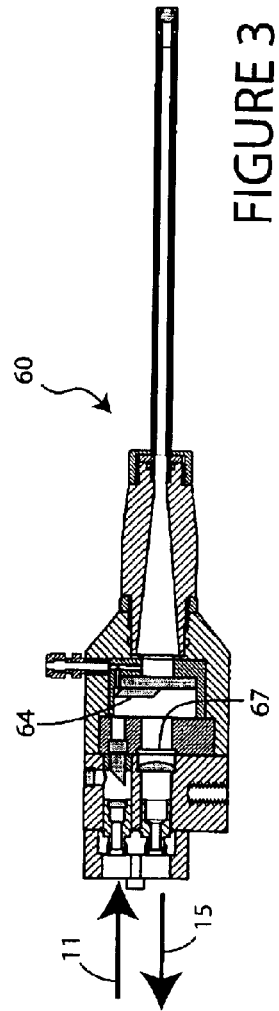
FIG. 3 is a sectional view of a second prior art Raman probe.
Figure 4:
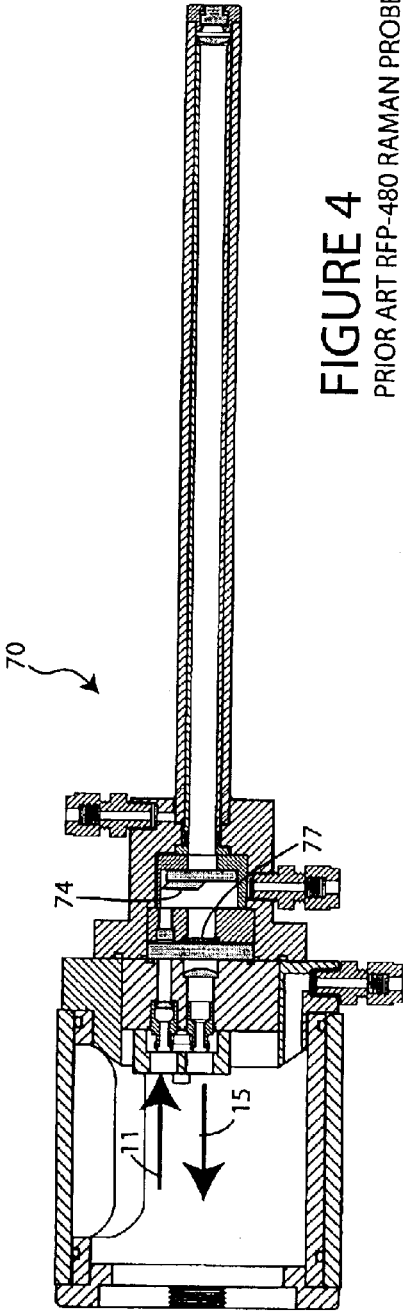
FIG. 4 is a sectional view of a third prior art Raman probe.

FIG. 13 shows a system 900 that a light guide 960 for a small diameter probe tip of the type illustrated in FIG. 3 above. In this embodiment, the purpose of the light guide 960 is not to contain the sample, but rather to confine the radiation to a small diameter region. The ultimate purpose is to provide a small diameter probe tip with a high ratio of length to diameter. The simplest embodiment would simply use the standard RFP-420 probe (FIG. 3) with a reflex mirror placed in or behind the sample (see e.g. the embodiment of FIGS. 15–17 discussed below). The position of the mirror 940 can be slightly defocused to increase the divergence of the reflected radiation, insuring that some of it misses the injection element 920. Alternatively, the embodiment of FIG. 13 can include a converging lens 930 to aid in injecting the excitation beam into the small diameter light guide 960. Any of the embodiments discussed above can also be combined with the small diameter light guide 960 as long as the physical parameters of the device can be met in manufacturing.

FIG. 14 shows one further embodiment of an alterative system 1000. In the embodiments discussed above, a plane mirror 140-940 is generally placed in or near the focal plane of the objective lens 130-930. In many cases, however, the plane mirror can be replaced by a concave spherical mirror 1040 with its center of curvature at or near the focal point of the lens 1030. This has the advantage of allowing Raman scattered radiation to be collected from regions on both forward and rearward sides of the focal point 1031.

In the plane mirror case of FIG. 7, offsetting the injection element 320 to one side allowed for four passes through the sample before the excitation beam returns to and rejoins the injection element. However, a concave mirror 1040 of FIG. 14, has the disadvantage of directing the first reflected or returned path beam toward the injection element 1020 as shown in FIG. 14. Of course, the various techniques discussed above can be used in conjunction with this embodiment to insure that at least part of the reflected signal misses the injection element 1020.

Figure 15:
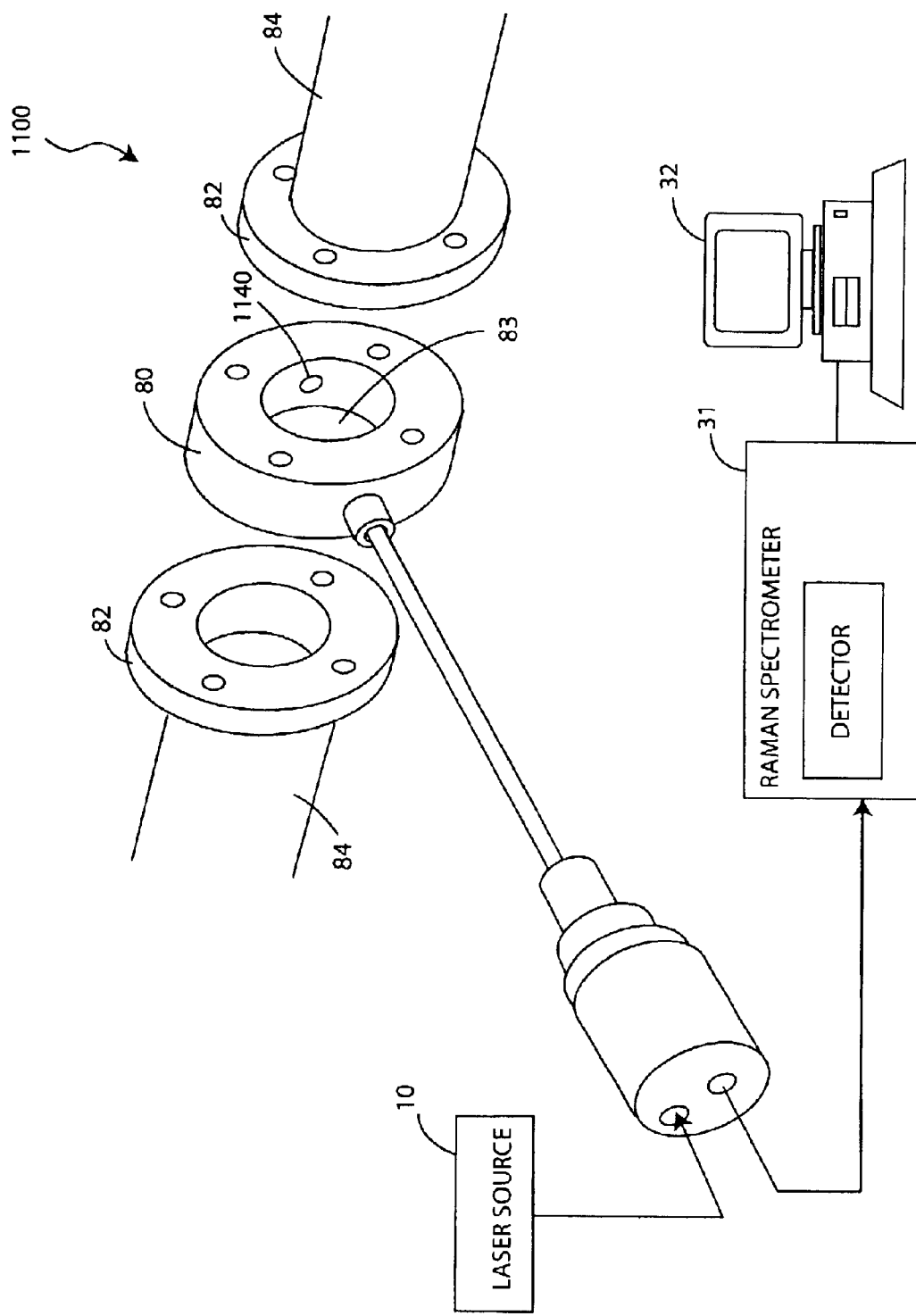
FIG. 15 is a perspective view of a multi-pass Raman sampling system 1100 that use an RFP-420 Raman probe 60 as illustrated in FIG. 3, in combination with a sample cell 80 having a flow aperture 83 and a mirror 1140.
Figure 16:
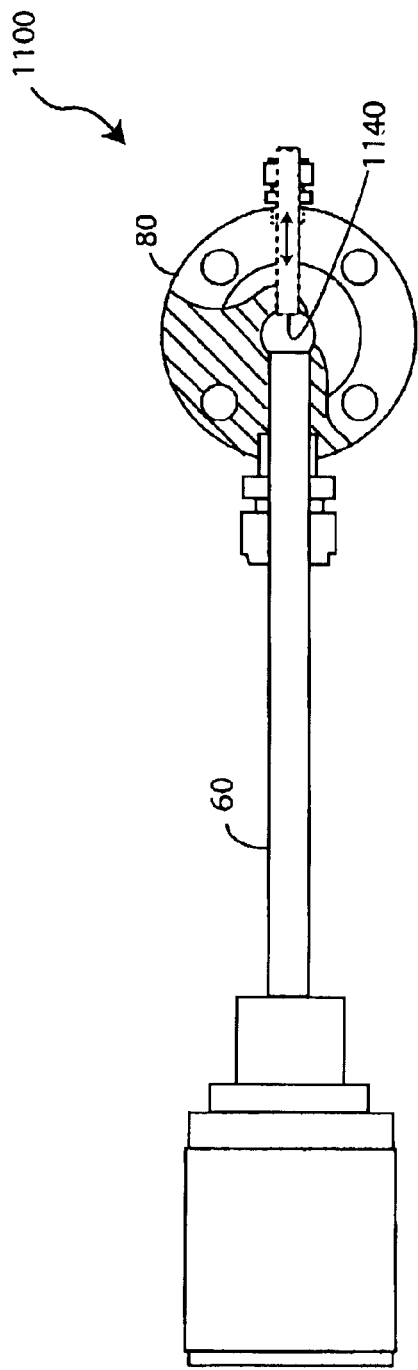
FIG. 16 is a cross-section of FIG. 15 taken from the side.
Figure 17:
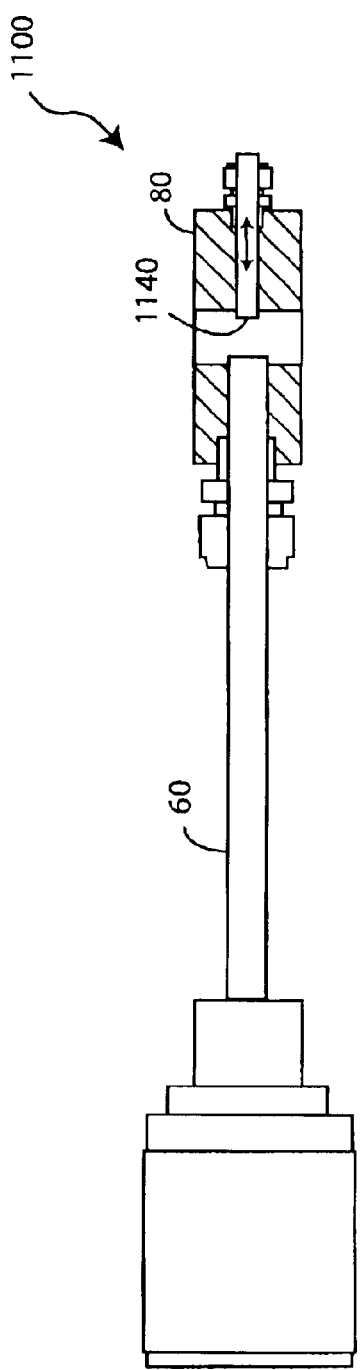
FIG. 17 is a cross-section of FIG. 15 taken looking down.

FIGS. 15–17 illustrate a particular application of a system 1100 wherein a RFP-420 Raman probe 60, as illustrated in FIG. 3, is combined with a sample cell 80 having a flow aperture 83. The flow cell 80 is connected to the flanges 82 of process or process development pipe 84. As with many of the above-described embodiments, a mirror 1040 is provided for creating a multi-pass Raman sampling system. As can be appreciated from FIG. 15, with the probe 60 and the mirror 1040 positioned correctly (note the arrows suggesting that it may be moved in and out of the focal plane), the excitation beam will make multiple passes through the passing sample and provide an enhanced Raman signal.

While the embodiments above have been described with respect to particular details shown in the figures, it is to be explicitly understood that there are many additional variations within the spirit and scope of the instant invention. Therefore, the invention is to be limited only by the following claims.

I claim:

1. A multi-pass Raman sampling system that illuminates a sample with laser excitation radiation to produce Raman shifted radiation, the system comprising:

an injection element located in an optical path, the injection element obscuring only a portion of the optical path while injecting a substantially collimated beam of laser excitation radiation toward the sample in a first direction;

an objective lens positioned in the optical path and defining an optical axis and a focal point, the objective lens focusing the collimated beam of laser excitation radiation traveling in the first direction into the sample to produce Raman shifted radiation, the objective lens collecting radiation that is emanating from at or near the focal point and then transmitting the radiation into the optical path in a second direction that is substantially opposite to the first direction;

a mirror located within or behind the sample at or near the focal point, the mirror reflecting both laser excitation radiation and Raman shifted radiation back through the sample toward the objective lens and the injection element in the second opposite direction;

a blocking filter located optically beyond the injection element such that the injection element is in the optical path between the objective lens and the blocking filter, the blocking filter being substantially reflective to the laser excitation radiation and substantially transparent to the Raman shifted radiation, the blocking filter passing the Raman shifted radiation out of the system for analysis and reflecting the laser excitation radiation back in the first direction toward the objective lens, the sample, and the mirror; and signal enhancement means for causing at least a portion of the laser excitation radiation that is reflected by the mirror to miss the injection element and strike the blocking filter where it is reflected back to the sample through the objective lens to produce further Raman shifted radiation.

2. The multi-pass Raman sampling system of claim 1 wherein the injection element comprises a separate pair of reflective surfaces.

3. The multi-pass Raman sampling system of claim 1 wherein the injection element comprises a rhomboid prism.

4. The multi-pass Raman sampling system of claim 1 wherein the signal enhancement means comprises optical beamspread of the substantially collimated beam of laser excitation radiation.

5. The multi-pass Raman sampling system of claim 4 wherein the optical beamspread is inherent.

6. The multi-pass Raman sampling system of claim 4 wherein the optical beamspread is induced.

7. The multi-pass Raman sampling system of claim 1 wherein the signal enhancement means comprises positioning the mirror to either side of the objective lens' focal point.

8. The multi-pass Raman sampling system of claim 1 wherein the signal enhancement means comprises the injection element being offset relative to the optical axis.

9. The multi-pass Raman sampling system of claim 8 wherein the signal enhancement means further comprises the blocking filter being tilted relative to the optical axis.

10. The multi-pass Raman sampling system of claim 8 wherein the signal enhancement means further comprises the offset injection element being tilted in a plane other than a plane in which the injection element is offset from the optical axis.

11. The multi-pass Raman sampling system of claim 1 wherein the signal enhancement means comprises the mirror being tilted relative to the optical axis.

12. The multi-pass Raman sampling system of claim 1 wherein the signal enhancement means comprises the blocking filter being titled relative to the optical axis.

13. The multi-pass Raman sampling system of claim 1 wherein the signal enhancement means comprises a lightguide located between the injection element and the objective lens.

14. The multi-pass Raman sampling system of claim 1 wherein the mirror is a planar mirror.

15. multi-pass Raman sampling system of claim 1 wherein the mirror is a concave spherical mirror with its center of curvature at or near the focal point of the objective lens.

16. The multi-pass Raman sampling system of claim 1 further comprising a hollow lightguide that forms a sample cell for holding the sample, wherein the sample cell has a window at one end for optically interfacing with the objective lens, and wherein the mirror is at an opposite end of the sample cell.

17. The multi-pass Raman sampling system of claim 16 wherein the injection element is offset relative to the optical axis.

18. The multi-pass Raman sampling system of claim 16 wherein the mirror located at the opposite end of the hollow lightguide is tilted relative to the optical axis.

19. A multi-pass sample interfacing system for use in Raman spectroscopy comprising:

means for directing a laser beam into a sample being analyzed;

means for collecting Raman scattered radiation produced in the sample and directing it on a path which is approximately parallel to and in the opposite direction from the laser beam;

an optical filter that is positioned to intercept the Raman scattered radiation, the optical filter being substantially perpendicular to a direction of propagation of the Raman scattered radiation, the optical filter reflecting laser radiation which strikes back toward the sample being analyzed; and a mirror located within or beyond the sample being analyzed and positioned approximately perpendicular to the direction of the laser beam so as to reflect radiation which strikes the mirror back through the sample being analyzed to the optical filter.

* * * * *